(12) United States Patent
Wilson et al.

(10) Patent No.: US 8,853,402 B2
(45) Date of Patent: Oct. 7, 2014

(54) PROCESS FOR REDUCING THE 6-KETO GROUP OF A MORPHINAN ALKALOID TO THE 6-HYDROXY GROUP BY HYDROGENATION

(75) Inventors: George Scott Wilson, Edinburgh (GB); Maureen Joan Young, Edinburgh (GB)

(73) Assignee: Johnson Matthey Public Limited Company, London (GB)

( * ) Notice: Subject to any disclaimer, the term of this patent is extended or adjusted under 35 U.S.C. 154(b) by 250 days.

(21) Appl. No.: 13/390,818

(22) PCT Filed: Aug. 13, 2010

(86) PCT No.: PCT/GB2010/051343
§ 371 (c)(1),
(2), (4) Date: May 2, 2012

(87) PCT Pub. No.: WO2011/021029
PCT Pub. Date: Feb. 24, 2011

(65) Prior Publication Data
US 2012/0209002 A1 Aug. 16, 2012

(30) Foreign Application Priority Data

Aug. 17, 2009 (GB) .................................. 0914338.9

(51) Int. Cl.
*C07D 489/08* (2006.01)
*C07D 489/02* (2006.01)

(52) U.S. Cl.
USPC ............................................. 546/44; 546/45

(58) Field of Classification Search
USPC ..................................................... 546/44, 45
See application file for complete search history.

(56) References Cited

U.S. PATENT DOCUMENTS

| | | | |
|---|---|---|---|
| 5,756,745 A | 5/1998 | Kavka | |
| 7,985,858 B2 * | 7/2011 | Grote et al. | 546/46 |
| 8,236,957 B2 * | 8/2012 | Rezaie et al. | 546/44 |

FOREIGN PATENT DOCUMENTS

| | | |
|---|---|---|
| GB | 1 366 931 | 9/1974 |
| WO | WO-2006/035195 A1 | 4/2006 |
| WO | WO-2008/137672 A1 | 11/2008 |
| WO | WO-2010/017573 A1 | 2/2010 |

OTHER PUBLICATIONS

Small et al., "The Addition of Organomagnesium Halides to Pseudocodeine Types. II. Preparation of Nuclear Alkylated Morphine Derivatives," *J. Am. Chem. Soc.*, 1936, vol. 58, pp. 1457-1463.
Findlay et al., "The Acid-catalyzed Conversion of Codeinone to 8-Hydroxydihydrocodeinone," *J. Am. Chem. Soc.*, 1951, vol. 73, pp. 4001-4004.
Goto et al., "(+)-Dihydrocodein and (+)-Dinydromorphin aus Sinomenin," *Justus Liebigs Annalen der Chemie*, 1941, vol. 547, pp. 194-200.
Findlay, "The Three-Dimensional Structures of the Cocaines. II. Racemic Allococaine and racemic Allopseudococaine," *J. Org. Chem.*, 1959, vol. 24, pp. 1540-1550.
Lutz et al, "Reduction Studies in the Morphine Series. IX. Hydroxycodeinone,"*J. Org. Chem.*, 1939, vol. 4, pp. 220-233.
Fujii et al., "Synthesis of N-isobutylnoroxymorphone from naltrexone by a selective cyclopropane ring opening reaction," *Bioorganic & Medicinal Chemistry Letters*, 2008, vol. 18, No. 18, pp. 4978-4981.
International Search Report dated Nov. 22, 2010, from International Application No. PCT/GB2010/051343.
British Search Report dated Nov. 26, 2009 from British Patent Application No. 0914338.9.

* cited by examiner

*Primary Examiner* — Charanjit Aulakh
(74) *Attorney, Agent, or Firm* — RatnerPrestia

(57) ABSTRACT

A process for the reduction of a 6-keto group in a morphinan alkaloid to the corresponding 6-hydroxy group includes hydrogenating the 6-keto group using gaseous hydrogen in the presence of a heterogeneous catalyst and a solvent, to yield the 6-hydroxy morphinan alkaloid, wherein the reduction is carried out at a pH in the range of about 5 to about 7, and the 6-hydroxy morphinan alkaloid has an $\alpha{:}\beta$ ratio of >85:15.

15 Claims, 1 Drawing Sheet

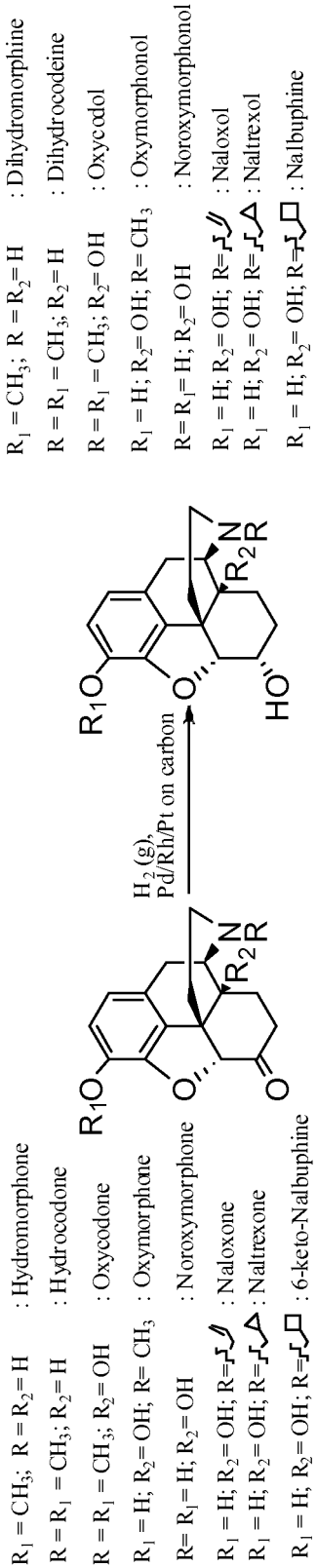

PROCESS FOR REDUCING THE 6-KETO GROUP OF A MORPHINAN ALKALOID TO THE 6-HYDROXY GROUP BY HYDROGENATION

CROSS-REFERENCE TO RELATED APPLICATIONS

This application is the U.S. National Phase filing of PCT International Application No. PCT/GB2010/051343, filed Aug. 13, 2010, and claims priority of British Patent Application No. 0914338.9, filed Aug. 17, 2009, the disclosures of both of which are incorporated herein by reference in their entireties for all purposes.

FIELD OF THE INVENTION

The present invention concerns an improved process for the synthesis of opiates, and more especially it concerns the reduction of a keto group in the 6-position of a morphinan alkaloid.

BACKGROUND OF THE INVENTION

Naltrexol has been proposed as a treatment for heroin dependency. 6-β-Naltrexol is the major metabolite of naltrexone. We are interested in finding industrially applicable routes to 6α-naltrexol. Molecules of similar structure include α-noroxymorphol and α-nalbuphine.

The state of the art process for the production of such compounds involves the reduction of a 6-keto group on the corresponding naltrexone, noroxymorphone or 6-keto-nalbuphine using a borohydride, especially at low temperatures. This process is described in U.S. Pat. No. 5,756,745 (Mallinckrodt). Such borohydride reductions have been found to be difficult to scale up to commercial scale production, there are safety issues associated with storing and using borohydrides and the by-product boron salts need to be removed from the product.

WO2006/035195 (Johnson Matthey) describes the conversion of noroxymorphone to nalbuphine by a hydrogenation using platinum on carbon catalyst, followed by sodium borohydride addition.

WO2008/137672 (Mallinckrodt) aims to avoid the use of borohydride by the use of a ruthenium, rhodium or iridium asymmetric catalyst in combination with a hydrogen source and a solvent. The typical chiral catalysts are Noyori catalysts. Hydrogen sources include gaseous hydrogen at up to 100 atm or, preferably, a hydrogen transfer agent such as isopropanol or formic acid. If isopropanol is used, a small amount of activator such as KOH may be added, but the preferred hydrogen source is a 5:2 mixture of formic acid and triethylamine. Yields are stated to be 83% for nalbuphine, with a 99:1 6α-nalbuphine to 6β-nalbuphine ratio.

There remains a need for simple and inexpensive reduction method for this transformation.

SUMMARY OF THE INVENTION

This invention therefore provides a process for the reduction of a 6-keto group in a morphinan alkaloid to the corresponding 6-hydroxy group, comprising hydrogenating the 6-keto group using gaseous hydrogen in the presence of a heterogeneous catalyst and a solvent, to yield the 6-hydroxy product.

The molecules to which this reduction can be applied are noroxymorphone, naltrexone, 6-keto-nalbuphine, hydromorphone, hydrocodone, oxycodone, oxymorphone and naloxone.

BRIEF DESCRIPTION OF THE DRAWING

FIG. 1 shows a reaction scheme suitable for practicing a process according to the invention.

DETAILED DESCRIPTION OF THE INVENTION

In brief, the process of the invention may be represented by the reaction scheme in FIG. 1.

The inventors have found that, although the heterogeneous catalyst is not asymmetric, the reduction may be stereoselective. In a preferred embodiment, the 6α-hydroxy stereoisomer is the major product. More preferably, the 6α-hydroxy group is produced in an α:β ratio of >85:15. For example, the 6α-hydroxy group is produced in an α:β ratio of 86:14. Even more preferably, the 6α-hydroxy group is produced in an α:β ratio of ≥90:10. For example, under desired conditions the 6α-hydroxy group is produced in an α:β ratio of ≥93:7. Even more preferably, the 6α-hydroxy group is produced in an α:β ratio of ≥94:6. For example, the 6α-hydroxy group is produced in an α:β ratio of ≥95:5. In one particularly preferred embodiment, an α:β ratio of 98:2 can be obtained. Resolution of the stereoisomers may readily be carried out using conventional HPLC methods.

The reduction is carried out in the presence of a heterogeneous catalyst. Preferably, the heterogeneous catalyst is a platinum group metal on a solid support. More preferably, the heterogeneous catalyst is selected from the group consisting of palladium on carbon, rhodium on carbon, platinum on carbon, iridium on carbon, ruthenium on carbon and mixtures thereof.

The catalyst loading may be up to about 10 mole %. In one embodiment, the catalyst loading may be up to 5 mole % concentration and, in one preferred embodiment, about 0.4-1.0 mole %. Sources of catalyst and sources of solid support do vary, and it is recommended that the catalyst is selected by conventional trial and error optimisation.

The hydrogen pressure is suitably in the range of up to about 100 psi and is suitably approximately 40 psi (about 2.758 bar).

If the alkaloid has one or more substituents which may be adversely affected during the reduction, such as 3-hydroxy or 14-hydroxy groups, these may be protected in a conventional manner. Alternatively, if these substituents have been protected prior to the hydrogenation reaction (for example, in steps leading to the synthesis of the 6-keto morphinan alkaloid), the protecting group(s) may be selected such that simultaneous hydrogenation of the 6-keto group and deprotection occurs. Suitable protecting groups which are capable of withstanding hydrogenation or are removed during hydrogenation are known in the art (see, for example, "Protective Groups in Organic Chemistry", Peter G. M. Wuts and Theodora W. Greene, Wiley Blackwell).

The inventors have identified that it is possible to carry out the hydrogenation at acidic, neutral or alkaline pHs. Preferably therefore the reduction may be carried out at a pH in the range of about 0 to about 13. A particularly preferred range is from about pH 5 to about 7. In this instance, the inventors have identified that it is possible to minimise the formation of the β stereoisomer and further improve the present process by minimising degradation and loss of yield.

In one embodiment, the process further comprises an acid. Preferably, the acid is an organic acid such as acetic acid, or an inorganic acid such as phosphoric acid, orthophosphoric acid or hydrochloric acid.

Any suitable solvent may be utilised e.g. aqueous solvents, polar solvents, aprotic dipolar solvents, non-polar solvents or mixtures thereof. In one embodiment, the solvent is suitably water, and desirably a co-solvent is used. The co-solvent may be a polar solvent, such as an alcohol. In this instance, the alcohol may be selected from the group consisting of methanol, ethanol, isopropanol and mixtures thereof. A preferred alcohol is isopropanol (IPA). Desirably, the quantity of isopropanol is kept at or below about 50 vol %, since conversion and the α:β ratio appear to be adversely affected with increasing isopropanol quantities above about 50 vol %. Alternatively, the co-solvent may be a non-polar solvent, such as an aromatic hydrocarbon e.g. toluene. In an embodiment, the solvent may be a mixture of polar solvents, such as a cyclic amide (e.g. N-methyl pyrrolidone) and an alcohol (e.g. methanol, ethanol or isopropanol, preferably methanol).

Reaction temperatures are suitably in the range from 20 to 75° C., preferably in the range from about 25 to about 60° C., most preferably about 35 to about 50° C.

The 6-keto group may be in a tautomeric equilibrium with its corresponding enol and a number of factors may influence this equilibrium. These factors include the pH or temperature at which the reduction is conducted, the solvent used or concentration of the morphinan alkaloid reactant. If the enol tautomer is present, however, its hydrogenation will still yield the desired 6-hydroxy morphinan alkaloid. As such, the present invention encompasses the reduction of the 6-keto group, the corresponding enol of the 6-keto group or a tautomeric mixture thereof.

It has been observed that the reduction of the 6-keto group in the morphinan alkaloid may be completed within about 24 hours and more preferably, within about 1 hour to about 8 hours.

The product may be isolated and purified using conventional techniques. For example, once the reduction is complete, work up may involve pH adjustment to ensure that the alkaloid components are in solution, followed by the removal of the catalyst by filtration, then basification of the filtrate to precipitate the alkaloid components, cooled (if necessary) and subsequently filtered and washed. Typical purification methods may involve one or more recrystallisations.

Acid addition salts of the 6-hydroxy morphinan alkaloid may be prepared if desired. In this instance, any suitable salt may be prepared, preferably a pharmaceutically acceptable salt. Hydrochloride salts are particularly preferred. Methods for preparing salts are well known to the skilled person. In an exemplary process, the 6-hydroxy morphinan alkaloid may be converted to its acid addition salt by heating a slurry of the 6-hydroxy morphinan alkaloid with an alcohol (e.g. ethanol) or alcohol/water mixture, adding the acid, followed by cooling and filtration. The salt may then be optionally recrystallised if desired.

The process of the present invention may additionally comprise a reductive alkylation reaction before, after or simultaneously with the reduction of the 6-keto group. WO2006/035195 (Johnson Matthey) relates to the reductive alkylation of morphinan alkaloids, the contents of which are incorporated herein by reference. In this instance, noroxymorphone and noroxymorphol are useful substrates as they may be alkylated to form a series of 14-hydroxylated opiate derivatives.

The invention will now be described by way of the following non-limiting Examples.

EXAMPLES

Example 1

Reduction of 6-ketonalbuphine to Generate Nalbuphine Alkaloid 6-ketonalbuphine (40 g, 112.8 mmoles) was dissolved in a mixture of IPA (200 mls) and water (200 mls) containing orthophosphoric acid (1.56 mls). The pH of the reaction mixture was 6.49. The reaction mixture was hydrogenated at 40 psi hydrogen gas and 50° C. in the presence of 10% Platinum on carbon catalyst (2.4 g, 0.56 mmoles Pt). After 7 hours, the pH of the reaction mixture is adjusted with orthophosphoric acid (6.25 mls) and filtered. Ammonia solution (25 mls) was added to bring the pH to 8.5-9.0 and the precipitate filtered, washed with 50% aqueous IPA (60 mls), and dried to provide 39.33 g (97% theory) of Nalbuphine alkaloid of purity 95.6% by HPLC.

Conversion of Nalbuphine Alkaloid to Nalbuphine Hydrochloride

Nalbuphine alkaloid (33.1 g) was charged to a flask containing ethanol (79 ml) and water (20 ml) and the mixture heated to 50° C. Concentrated Hydrochloric acid (9.1 mls) was added to adjust to within the pH range 4-4.5. The resulting solution was cooled to <10° C. using an ice bath and held for ~2 hours and filtered. The Nalbuphine hydrochloride solid was washed with ethanol:water (10.6 ml:2.6 ml) and dried at 55° C. in a fan oven to afford 35.27 g (89% theory) of Nalbuphine hydrochloride.

Example 2

Reduction of Hydromorphone to Generate Dihydromorphine

Hydromorphone (10 g) was charged to a Parr hydrogenator flask followed by IPA (50 ml), water (50 ml), and orthophosphoric acid (0.37 ml). 10% Pt/C catalyst (1.49 g) were added and the mixture hydrogenated at 50° C. and 40 psi hydrogen for 1 hour when HPLC (against a reference standard) showed the mixture to comprise solely dihydromorphine.

Example 3

Reduction of Noroxymorphone to Generate Noroxymorphol

Noroxymorphone alkaloid (2 g) was charged to a flask containing water (5 ml), and hydrochloric acid (0.43 mls). Rh/C catalyst (1 mole %) was added and the reaction hydrogenated at 40 psi hydrogen and 35° C. for 7 hours. HPLC analysis indicated a 98% conversion to Noroxymorphol with an α:β ratio of diastereomers of 95:5.

Example 4

Reduction of Naltrexone to Generate Naltrexol

Naltrexone (20.0 g), IPA (100 ml), water (100 ml) and $H_3PO_4$ (0.6 ml) were charged to a 250 ml reaction flask and heated to 50° C. 10% Pt/C catalyst (1.3 g) was added and the reaction hydrogenated at 50° C. and 40 psi for a period of 7 hrs. Harborlite (0.2 g) was added and the batch filtered to remove catalyst residues. Ammonia solution (2 mls) was added to adjust the pH to 8.0-9.0 whereupon the mixture was cooled to <10° C., filtered, washed with water (20 mls), and dried at 55° C. 11.16 g (55.5% yield) of a beige solid, corresponding to α-Naltrexol by HPLC was obtained. $^1$H NMR (CDCl$_3$ δ/ppm) 0.00 (4H, m), 0.39 (4H, m), 0.70 (2H, m), 1.00 (2H, m), 1.30 (2H, m), 1.51 (6H, m), 2.10 (4H, m), 2.20 (4H, m), 2.45 (4H, m), 3.41 (1H, m), 4.15 (1H, m), 4.41 (1H, d, J=6 Hz), 4.55 (1H, d, J=6 Hz), 6.35 (1H, d, J=10 Hz), 6.55 (1H, d, J=10 Hz), 5.10-5.70 (6H, very broad s). $^{13}$C NMR (CDCl$_3$ δ/ppm) 3.86, 4.09, 9.45, 22.89, 23.20, 28.91, 33.46, 43.28, 47.50, 59.65, 62.16, 67.02, 70.13, 90.74, 117.92, 119.2, 125.5, 131.1, 137.7, 145.9

Example 5

Reduction of Hydrocodone to Generate Dihydrocodeine

Hydrocodone (10 g) was charged to a Parr hydrogenator flask followed by water (50 ml), IPA (50 ml) and phosphoric acid (0.3 ml). 10% Pt/C catalyst (1.42 g) was added and the mixture hydrogenated at 50° C. and 40 psi hydrogen. Hydrogen uptake was observed to cease after 5 hours and harborlite added to the crude reaction mixture which was then filtered. HPLC analysis indicated that the major product formed correlated with a dihydrocodeine reference standard.

Example 6

Reduction of Oxycodone to Generate Oxycodol

Oxycodone (5 g) was charged to a Parr hydrogenator flask followed by water (50 ml), and hydrochloric acid (0.3 ml). 10% Rh/C catalyst (1.51 g) was added and the mixture hydrogenated at 35° C. and 40 psi hydrogen. Hydrogen uptake was observed to cease after 6 hours and harborlite added to the crude reaction mixture which was then filtered. HPLC analysis indicated that the major product formed correlated with a oxycodol reference standard.

Example 7

Telescope of the Reductive Alkylation & Asymmetric Ketone Reduction Reactions (Naltrexol)

Noroxymorphone (10 g, 34.8 mmoles) were charged to a hydrogenator flask along with NMP (30 mls) and Methanol (70 mls), and cyclopropane carboxaldehyde (2.5 mls, 38.5 mmoles). 5% Pt/C (0.32 g) was added and the mixture hydrogenated under 40 psi hydrogen gas for 3 hours. Harborlite (0.2 g) was added and the mixture filtered. Water (100 mls) was added to the filtered reaction solution and the resulting slurry was cooled to 0-5° C. The precipitate was removed by filtration and stored until recombined with toluene extracts (150 mls) obtained from extracting active material from the filtrate with toluene (5×30 mls). The combined toluene extracts were then washed with water (5×30 mls) and recombined with the previously filtered solid precipitate. A solution of aqueous acetic acid (80 mls, 1.6%) was then added to the reaction slurry in toluene and heated to 50° C. Once all the solid was dissolved (10 minutes), the two layers were separated and the aqueous later cooled to 20-30° C. 5% Pt/C catalyst (2.83 g) was added and the mixture hydrogenated at 50° C. and 40 psi for 2 hours. HPLC analysis showed the major product formed to be α-Naltrexol.

Example 8

One Pot Reductive Alkylation & Asymmetric Ketone Reduction Reactions (Naltrexol)

Noroxymorphone (10 g, 34.8 mmoles) were charged to a hydrogenator flask along with NMP (30 mls) and Methanol (70 mls), and cyclopropane carboxaldehyde (2.5 mls, 38.5 mmoles). 5% Pt/C (0.32 g) was added and the mixture hydrogenated under 40 psi hydrogen gas for 3 hours. Harborlite (0.2 g) was added and the mixture filtered. A fresh charge of 5% Pt/C (2.7 g) was added to the mixture which was then hydrogenated at 50° C. and 40 psi hydrogen for 2 hours. HPLC analysis showed the reaction solution to contain α-Naltrexol.

Example 9

One Pot Reductive Alkylation & Asymmetric Ketone Reduction Reactions (Nalbuphine)

Noroxymorphone (2 g, 6.9 mmoles) were charged to a hydrogenator flask along with NMP (6 mls) and Methanol (14 mls), and cyclobutane carboxaldehyde (0.67 mls). 5% Pt/C (3.15 g) was added and the mixture hydrogenated under 40 psi hydrogen at 50° C. for 3 hours. At the end of the reaction, HPLC analysis against a reference sample showed α-Nalbuphine to be the major product formed.

Example 10

α:β Ratio of 6-Hydroxy Morphinan Alkaloids

The table below details the α:β ratio of 6-hydroxy morphinan alkaloids produced according to the process of the present invention.

| 6-Keto Morphinan Alkaloid | 6-Hydroxy Morphinan Alkaloid | Catalyst | α:β Ratio of 6-Hydroxy Morphinan Alkaloid |
|---|---|---|---|
| Oxycodone | Oxycodol | Rh/C | 93:7 |
| 6-Keto-nalbuphine | Nalbuphine | Pt/C | 95:5 |
| Naltrexone | Naltrexol | Rh/C | 94:6 |
| Naltrexone | Naltrexol | Pt/C | 93:7 |
| Noroxymorphone | Noroxymorphol | Rh/C | 95:5 |
| Noroxymorphone | Noroxymorphol | Pt/C | 86:15 |
| Hydrocodone | Dihydrocodeine | Pt/C | 98:2 |
| Hydromorphone | Dihydromorphine | Pt/C | 98:2 |

The HPLC method used to determine the α:β ratio is as follows and is based on the European Pharmacopoeia method for naloxone hydrochloride:

| | |
|---|---|
| Column | Zorbax Eclipse XDB-C8 5 microns 12.5 cm × 4.0 mm |
| Mobile Phase | Prepare a solution as follows: dissolve 1.17 g sodium octansulphonate in 1000 ml water, adjust to pH 2.0 with a 50% v/v solution of phosphoric acid |
| | A 20 ml acetonitrile, 40 ml THF and 940 ml of above solution |
| | B 170 ml acetonitrile, 40 ml THF and 790 ml of above solution |
| Flow rate | 1.5 ml/minute |
| Temperature | 40° C. |
| Detector | UV @ 230 nm |
| Injection volume | 20 microlitres |
| Run time | 45 minutes |

Linear Gradient:

| Time (min) | A % v/v | B % v/v |
|---|---|---|
| 0 | 100 | 0 |
| 40 | 0 | 100 |
| 50 | 0 | 100 |
| 55 | 100 | 0 |
| 65 | 100 | 0 |

The invention claimed is:

1. A process for the reduction of a 6-keto group in a morphinan alkaloid to the corresponding 6-hydroxy group, wherein the 6-keto morphinan alkaloid is selected from the group consisting of noroxymorphone, naltrexone, 6-keto-nalbuphine, hydromorphone, hydrocodone, oxycodone, oxymorphone and naloxone, comprising hydrogenating the 6-keto group using gaseous hydrogen in the presence of a heterogeneous catalyst and one or more solvents, to yield the 6-hydroxy morphinan alkaloid,
wherein the reduction is carried out at a pH in the range of about 5 to about 7, and the 6-hydroxy morphinan alkaloid has an $\alpha$:$\beta$ ratio of >85:15.

2. The process according to claim 1, wherein the heterogeneous catalyst is a platinum group metal on a solid support.

3. The process according to claim 2, wherein the heterogeneous catalyst is selected from the group consisting of palladium on carbon, rhodium on carbon, platinum on carbon, iridium on carbon, ruthenium on carbon and mixtures thereof.

4. The process according to claim 1, wherein an acid is present during the hydrogenating.

5. The process according to claim 4, wherein the acid is selected from the group consisting of phosphoric acid, orthophosphoric acid, acetic acid, hydrochloric acid and mixtures thereof.

6. The process according to claim 1, wherein the one or more solvents are selected from the group consisting of an aqueous solvent, a polar solvent, an aprotic dipolar solvent, a non-polar solvent and mixtures thereof.

7. The process according to claim 6, wherein the one or more solvents comprises water.

8. The process according to claim 7, the one or more solvents further comprising a co-solvent selected from the group consisting of a polar solvent, a non-polar solvent and mixtures thereof.

9. The process according to claim 6, wherein the one or more solvents comprise an alcohol and/or a cyclic amide.

10. The process according to claim 6, wherein the one or more solvents comprise an aromatic hydrocarbon.

11. The process according to claim 1, wherein the process is carried out at a temperature in the range from about 20° C. to about 75° C.

12. The process according to claim 1, further comprising resolution of the 6$\alpha$ and 6$\beta$ stereoisomers by HPLC.

13. The process according to claim 1, further comprising a reductive alkylation reaction before, after or simultaneously with the hydrogenation of the 6-keto group.

14. The process according to claim 7, the one or more solvents further comprising a co-solvent selected from the group consisting of alcohols and cyclic amides.

15. The process according to claim 7, the one or more solvents further comprising a co-solvent selected from the group consisting of aromatic hydrocarbons.

* * * * *